United States Patent
Grob et al.

(10) Patent No.: US 7,922,766 B2
(45) Date of Patent: Apr. 12, 2011

(54) METHOD FOR RESURFACING A CERVICAL ARTICULAR FACET

(75) Inventors: Dieter Grob, Erlenbach (CH); Horace Winston Hale, Degersheim (CH)

(73) Assignee: Gerraspine A.G., St. Gallen (CH)

( * ) Notice: Subject to any disclaimer, the term of this patent is extended or adjusted under 35 U.S.C. 154(b) by 0 days.

(21) Appl. No.: 11/684,202

(22) Filed: Mar. 9, 2007

(65) Prior Publication Data

US 2007/0179619 A1 Aug. 2, 2007

Related U.S. Application Data

(62) Division of application No. 10/762,008, filed on Jan. 21, 2004, now abandoned.

(51) Int. Cl.
*A61F 2/44* (2006.01)
(52) U.S. Cl. ............... 623/17.11; 606/247; 606/280
(58) Field of Classification Search .......... 606/246–249; 623/17.11, 17.15
See application file for complete search history.

(56) References Cited

U.S. PATENT DOCUMENTS

| | | |
|---|---|---|
| 3,879,767 A | 4/1975 | Stubstad |
| 4,001,896 A | 1/1977 | Arkangel |
| 4,085,466 A | 4/1978 | Goodfellow |
| 4,502,161 A | 3/1985 | Wall |
| 4,714,469 A | 12/1987 | Kenna |
| 4,772,287 A | 9/1988 | Ray et al. |
| 4,773,402 A | 9/1988 | Asher et al. |
| 4,904,260 A | 2/1990 | Ray et al. |
| 4,936,848 A | 6/1990 | Bagby |
| 5,000,165 A | 3/1991 | Watanabe |
| 5,127,912 A | 7/1992 | Ray et al. |
| 5,360,431 A | 11/1994 | Puno et al. |
| 5,527,312 A | 6/1996 | Ray |
| 5,527,314 A | 6/1996 | Brumfield et al. |
| 5,571,191 A | 11/1996 | Fitz |
| 5,586,989 A * | 12/1996 | Bray, Jr. ............... 606/160 |
| 5,591,165 A | 1/1997 | Jackson |
| 5,707,373 A | 1/1998 | Sevrain et al. |
| 6,014,588 A | 1/2000 | Fitz |
| RE36,758 E | 6/2000 | Fitz |
| 6,132,464 A | 10/2000 | Martin |
| 6,565,605 B2 | 5/2003 | Goble et al. |

(Continued)

FOREIGN PATENT DOCUMENTS

DE 9304368.4 * 3/1993 ............ 606/247

(Continued)

OTHER PUBLICATIONS

Chiu, J.C., Davis, G.W., Clifford, T., And Greenspan M. Translaminar Facet Screw Fixation [retreived on May 27, 2003]. Retrieved from the Internet:<http://www.spinecenter.com/papers/facet/facet.htm.

(Continued)

*Primary Examiner* — Eduardo C Robert
*Assistant Examiner* — Mary Hoffman
(74) *Attorney, Agent, or Firm* — Renner Otto Boisselle & Sklar LLP

(57) ABSTRACT

Methods for treating spinal pathologies, and more specifically methods for treating articulating surfaces of facet joints of cervical vertebrae. The methods involve providing artificial articulating surfaces for facet joint articular facets. In addition, various types of rasps may be used to prepare the articulating surfaces prior to placement of the artificial articulating surfaces.

23 Claims, 8 Drawing Sheets

U.S. PATENT DOCUMENTS

| | | | |
|---|---|---|---|
| 6,579,319 B2 | 6/2003 | Goble et al. | |
| 6,589,244 B1 | 7/2003 | Sevrain et al. | |
| 6,610,091 B1 | 8/2003 | Reiley | |
| 6,669,729 B2 | 12/2003 | Chin | |
| 6,811,567 B2 | 11/2004 | Reiley | |
| 7,051,451 B2 | 5/2006 | Augostino et al. | |
| 7,074,238 B2 | 7/2006 | Stinson et al. | |
| 2002/0065557 A1 | 5/2002 | Goble et al. | |
| 2002/0123806 A1 | 9/2002 | Reiley | |
| 2002/0151895 A1 | 10/2002 | Soboleski et al. | |
| 2003/0004572 A1 | 1/2003 | Goble et al. | |
| 2003/0028250 A1 | 2/2003 | Reiley et al. | |
| 2003/0187454 A1 | 10/2003 | Gill et al. | |
| 2003/0216669 A1* | 11/2003 | Lang et al. | 600/587 |
| 2004/0127989 A1 | 7/2004 | Dooris et al. | |
| 2004/0230201 A1 | 11/2004 | Yuan et al. | |
| 2004/0230304 A1 | 11/2004 | Yuan et al. | |
| 2005/0015146 A1 | 1/2005 | Louis et al. | |
| 2005/0043797 A1 | 2/2005 | Lee | |
| 2005/0043799 A1 | 2/2005 | Reiley | |
| 2005/0055096 A1 | 3/2005 | Serham et al. | |
| 2005/0131538 A1 | 6/2005 | Chervitz et al. | |
| 2005/0197700 A1 | 9/2005 | Boehem et al. | |
| 2006/0149375 A1 | 7/2006 | Yuan et al. | |

FOREIGN PATENT DOCUMENTS

| | | | | |
|---|---|---|---|---|
| DE | 10135771 | * | 2/2003 | 606/247 |
| EP | 0 322 334 | | 6/1989 | |
| EP | 0 392 124 | | 10/1990 | |
| EP | 0 610 837 | | 8/1994 | |
| WO | 93/14721 | | 8/1993 | |
| WO | WO 03/101350 A1 | | 12/2003 | |

OTHER PUBLICATIONS

Nabil A. Ebraheim, Rongming Xu, Eric Challgren, and Richard A. Yeasting, Journal of Spiral Disorders, "Quantitative Anatomy of the Cervical Facet and the Posterior Projection of Its Inferior Facet," vol. 10, No. 4, pp. 308-316, 1997.

Jan P.J. van Schaik and Bart van Pinxteren, Journal of Spinal Disorders, "Curvature of the Lower Lumbar Facet Joints: Variations at Different Levels and Relationship with Orientation," vol. 12, No. 4, pp. 341-347, 1999.

Jike Lu, M.D., Nabil A. Ebraheim, M.D., and Richard A. Yeasting, PhD, The American Journal of Orthopedics, "Translaminar Facet Screw Placement: an Anatomic Study," pp. 550-555, Aug. 1999.

Nabil A. Ebraheim, M.D., Rongming Xu, M.D., Huhammad Ahmad, M.D. and Richard A. Yeasting, PhD, "The Quantitative Anatomy of the Thoracic Facet and the Posterior Projection of Its Inferior Facet," SPINE vol. 22, No. 16, pp. 1811-1818, 1997.

Manohar M. Panjabi, PhD, Thomas Oxland, MASc, Koichiro Takata, M.D., Vijay Goel, PhD, Joanne Duranceau, M.S. and Martin Krag, M.D., "Articular Facets of the Human Spine, Quantitative Three-Dimensional Anatomy," Spine vol. 18, No. 10, pp. 1298-1310, 1993.

Scott D. Boden, M.D., K. Daniel Riew, M.D., Ken Yamaguchi, M.D., Thomas P. Branch, M.D., Dieter Schellinger, M.D., and Sam W. Wiesel, Atlanta Georgia, "Orientation of the Lumbar Facet Joints: Association with Degenerative Disc Disease," The Journal of Bone and Joint Surgery, Inc., vol. 78-A, No. 3, Mar. 1996.

John M Cavanaugh, A. Cuneyt Ozaktay, H. Toshihiko Yamashita, and Albert I. King, "Lumbar Facet Pain: Biomechanics Neuroanatomy and Neurophysiology," Survey Article, J. Biomechanics, vol. 29, No. 9, pp. 1117-1129, 1996.

Nararyan Yoganandan, PhD., Stephanie A. Knowles, M.S., Dennis J. Maiman, M.D., PhD and Frank A. Pintar, PhD. "Anatomic Study of the Morphology of Human Cervical Facet Joint," SPINE, vol. 28, No. 20, pp. 2317-2323, © 2003, Lippincott Williams & Wilkins, Inc.

Dudley, Hugh A.F., ed., Carter, David C., ed. And Russell, R.C.G., ed., "Spinal Injuries," Rod & Smith's Operative Surgery—Orthopaedics Part 1, London: Butterworth-Heinemann, 1991, p. 641.

* cited by examiner

METHOD FOR RESURFACING A CERVICAL ARTICULAR FACET

CROSS-REFERENCE TO RELATED APPLICATION

This application is a divisional application of U.S. Application Ser. No. 10/762,008, filed Jan. 21, 2004 now abandoned, which is incorporated by reference.

FIELD OF THE INVENTION

The present invention relates generally to prostheses for treating spinal pathologies, and more specifically to a system and method for treating articulating surfaces of cervical facet joints.

BACKGROUND OF THE INVENTION

Back and neck pain are common ailments. In many cases, the pain severely limits a person's functional ability and quality of life. A variety of spinal pathologies can lead to back pain.

Through disease or injury, the laminae, spinous process, articular processes, or facets of one or more vertebral bodies can become damaged, such that the vertebrae no longer articulate or properly align with each other. This can result in an undesired anatomy, loss of mobility, and pain or discomfort. With respect to vertebral articular surface degeneration, facet joints may show a reduced thickness of cartilage and may advance to entire disappearance thereof. Furthermore, surrounding the degenerated articular surfaces, there is bony formation capable of causing neurological compressions inside either the foramenae or spinal canal. These facts induce pain which affect a large part of the population.

The vertebral facet joints, for example, can be damaged by either traumatic injury or by various disease processes, such as osteoarthritis, ankylosing spondylolysis, and degenerative spondylolisthesis. The damage to the facet joints often results in pressure on nerves, also called a "pinched" nerve, or nerve impingement. The result is pain, misaligned anatomy, and a corresponding loss of mobility. Pressure on nerves can also occur without facet joint pathology, e.g., a herniated disc.

Degenerative spinal diseases can involve articular surfaces only, but may also have a more invasive pathology including traumatic, infectious, tumorous or dysmorphic (spondylolisthesis, for example) effecting the destruction of all or part of the articular process. The locking of vertebral motions by spinal arthrodesis or ligamentoplasty induces, beyond a spinal stiffness, an increased force on the joint facets of the adjacent vertebrae above and below the fusion, usually sustained by the considered intervertebral space and therefore an increase of degeneration of these joint facets.

One type of conventional treatment of facet joint pathology is spinal stabilization, also known as intervertebral stabilization. By applying intervertebral stabilization, one can prevent relative motion between the vertebrae. By preventing this movement, pain can be reduced. Stabilization can be accomplished by various methods. One method of stabilization is spinal fusion. Another method of stabilization is fixation of any number of vertebrae to stabilize and prevent movement of the vertebrae. Yet another type of conventional treatment is decompressive laminectomy. This procedure involves excision of the laminae to relieve compression of nerves. With regard to discal prostheses, they provide a "space" between two vertebral bodies while preserving some motion. They solve the aging intervertebral disc problem but do not function to reduce the force on posterior joint facets.

These traditional treatments are subject to a variety of limitations and varying success rates. Furthermore, none of the described treatments puts the spine in proper alignment or returns the spine to a desired anatomy. In addition, stabilization techniques, by holding the vertebrae in a fixed position, permanently limit a person's mobility. Some procedures involving motion devices have a high incidence of spontaneous fusion. There is thus a need in the art for a system and procedure capable of increasing the percentage of good results in disc replacement surgery. In addition, there is a need in the art for better results than are commonly achieved through spinal fusions. Further, there is a need in the art for a system and procedure that permits greater mobility in cases of spinal problems involving only the facet joints, and for obviating the need for spinal fusion associated with degenerative and congenital problems of the spine.

BRIEF SUMMARY OF THE INVENTION

Disclosed is a method for providing articulating surfaces for cervical vertebrae facet joint articular facets. The method comprises creating a space between a superior articular facet of a selected cervical vertebra and an inferior articular facet of a cervical vertebra immediately above the selected vertebra; using an inferior facet rasp to prepare an articulating surface of the inferior articular facet for an inferior implant having an articulating surface and a fixation surface; using a superior facet rasp to prepare an articulating surface of the superior articular facet for a superior implant having an articulating surface and a fixation surface; fixing the inferior implant on the inferior articular facet such that the fixation surface of the inferior implant interacts with the articulating surface of the inferior articular facet; and fixing the superior implant on the superior articular facet such that the fixation surface of the superior implant interacts with the articulating surface of the superior articular facet. In addition, the articulating surface of the superior implant and the articulating surface of the inferior implant are positioned to articulate with one another following the fixation of the superior implant to the superior articular facet and fixation of the inferior implant to the inferior articular facet.

Also disclosed is another method for providing articulating surfaces for cervical vertebrae facet joint articular facets. The method comprises creating a space of from about 4 mm to about 15 mm between a superior articular facet of a selected cervical vertebra and an inferior articular facet of a cervical vertebra immediately above the selected vertebra; placing a generally disk-shaped inferior implant having an articulating surface and a fixation surface in the created space; fixing the inferior implant on the inferior articular facet such that the fixation surface of the inferior implant interacts with an articulating surface of the inferior articular facet; placing a generally disk-shaped superior implant having an articulating surface and a fixation surface in the created space; and fixing the superior implant on the superior articular facet such that the fixation surface of the superior implant interacts with an articulating surface of the superior articular facet. In addition, the articulating surface of the superior implant and the articulating surface of the inferior implant are positioned to articulate with one another following the fixation of the superior implant to the superior articular facet and fixation of the inferior implant to the inferior articular facet.

DETAILED DESCRIPTION OF THE INVENTION

Figure 1:
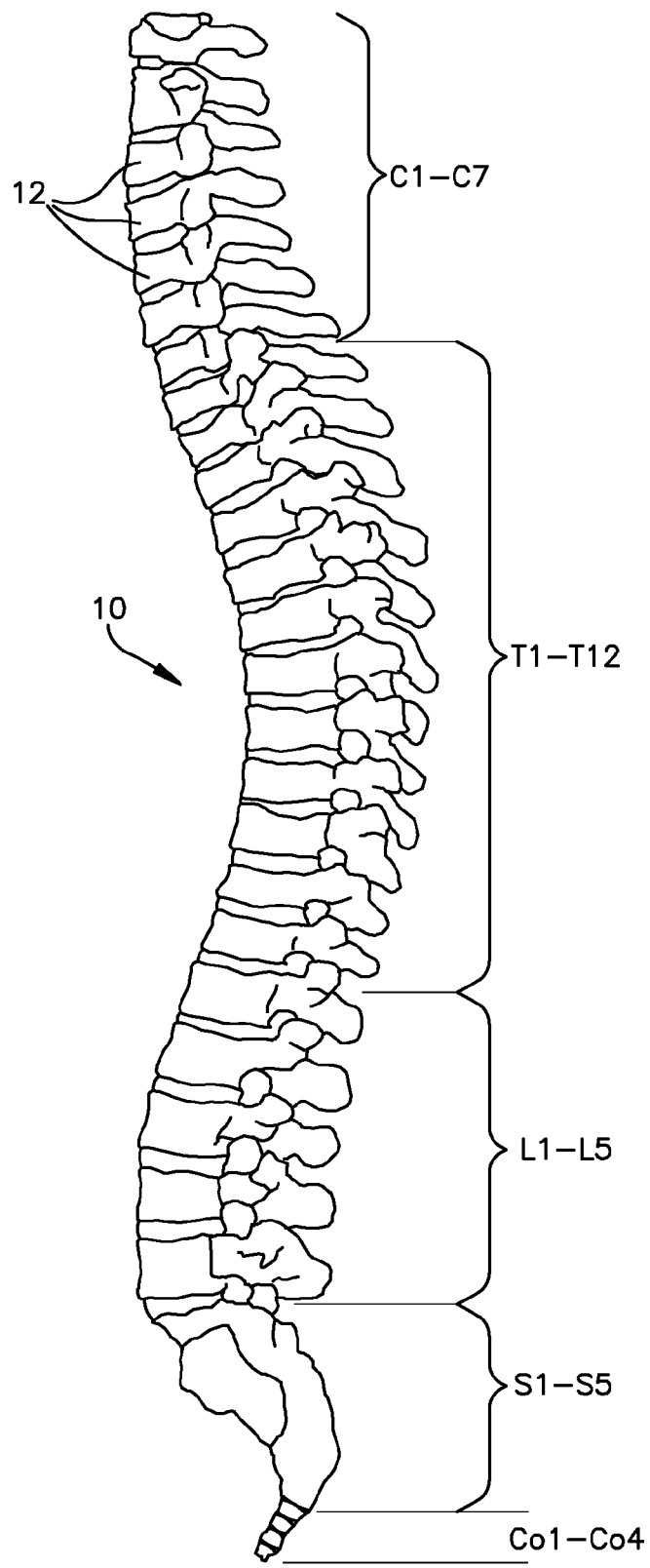
FIG. 1 is a lateral elevation view of a normal human spinal column.

Referring initially to FIG. 1, the human spinal column 10 is illustrated. The spinal column 10 is comprised of a series of thirty-three stacked vertebrae divided into five regions. The cervical region includes seven vertebrae, known as C1-C7. The thoracic region includes twelve vertebrae, known as T1-T12. The lumbar region contains five vertebrae, known as L1-L5. The sacral region is comprised of five vertebrae, known as S1-S5. The coccygeal region contains four vertebrae 12, known as Co1-Co4.

Figure 2A:
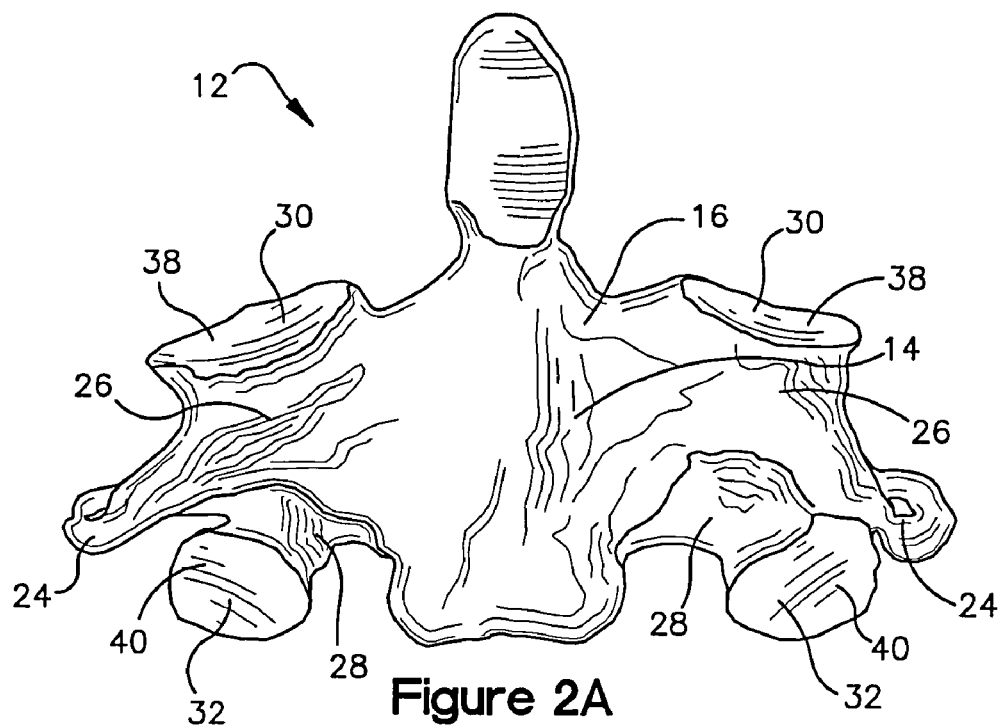
FIG. 2A is an anterior view of a normal human cervical vertebra.
Figure 2B:
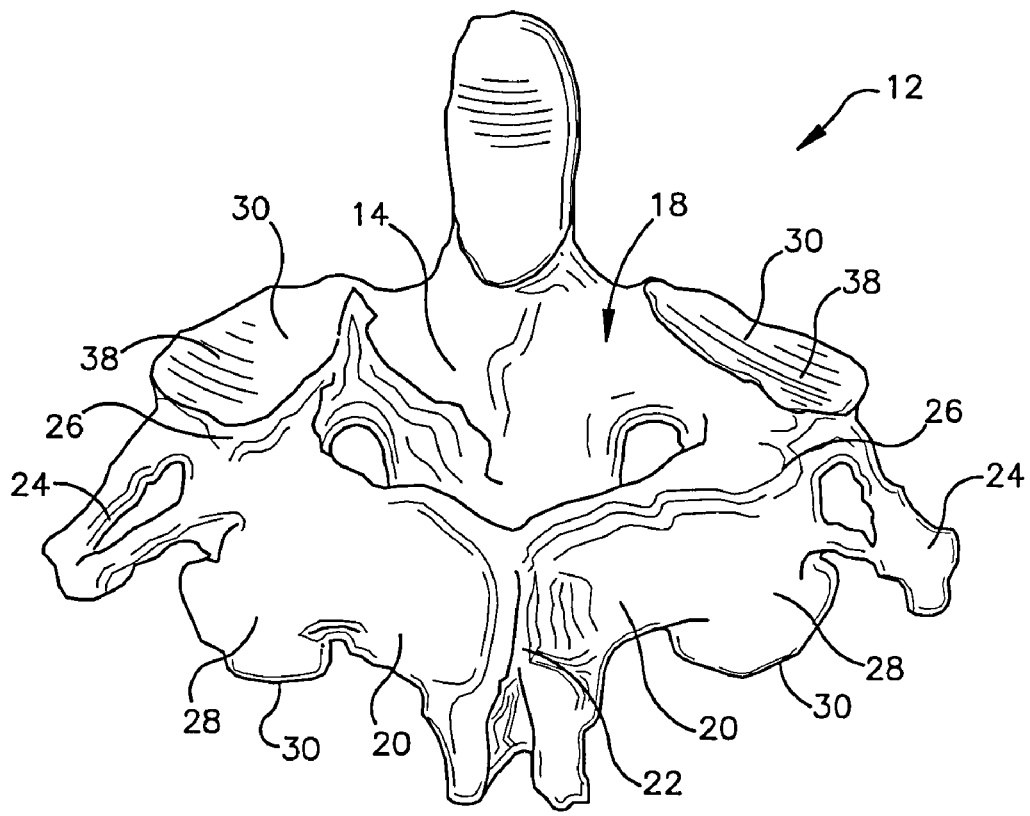
FIG. 2B is a posterosuperior view of a normal human cervical vertebra.
Figure 3:
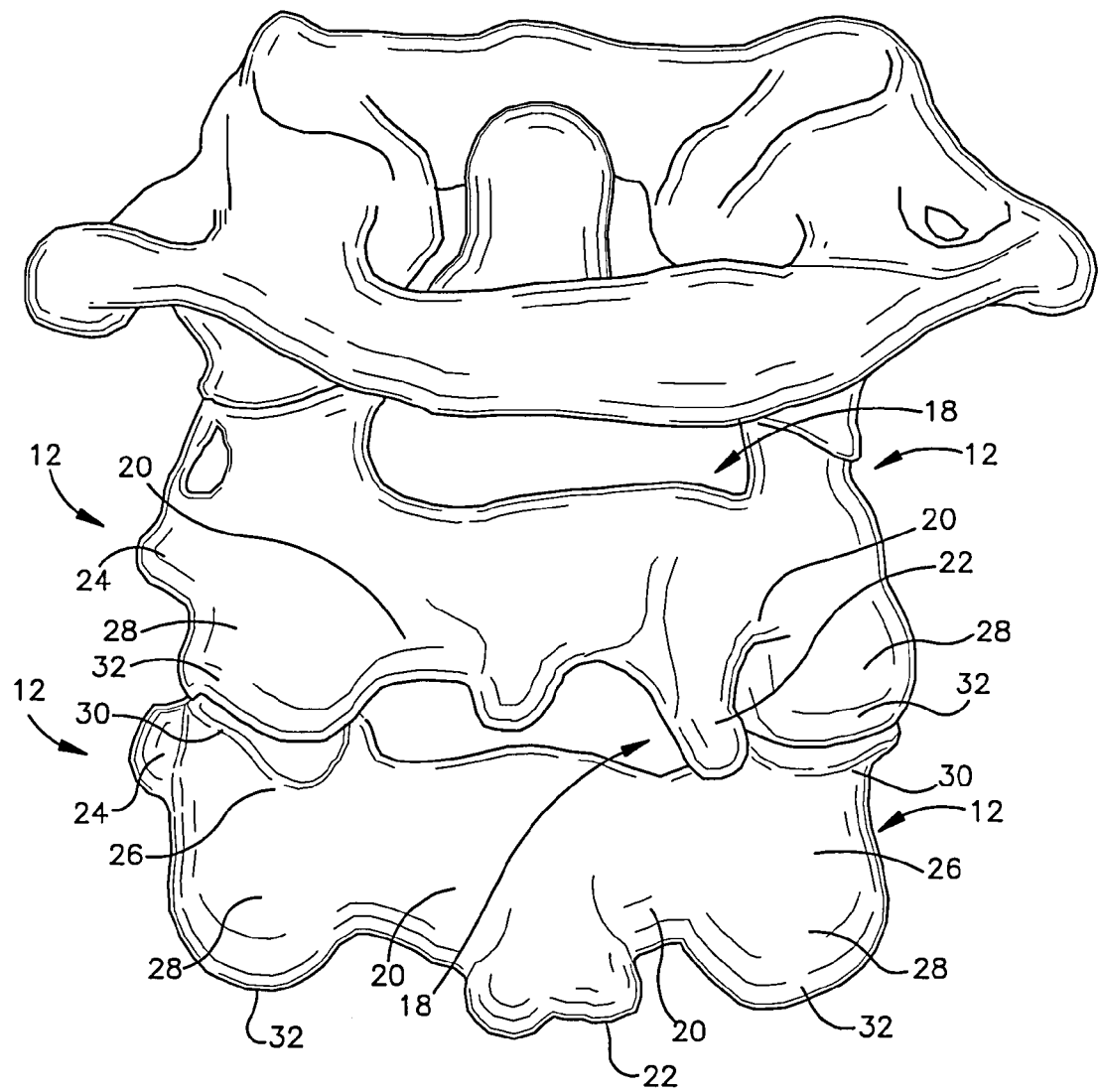
FIG. 3 is a posterior perspective view of a cervical vertebral facet joint.

Turning now to FIGS. 2 and 3, normal human cervical vertebrae 12 are illustrated. It will be understood by those skilled in the art that while the cervical vertebrae 12 vary somewhat according to location, they share many features common to most vertebrae 12. Each vertebra 12 includes a vertebral body 14. Two short bones, the pedicles 16, extend backward from each side of the vertebral body 14 to form a vertebral arch 18. At the posterior end of each pedicle 16, the vertebral arch 18 flares out into broad plates of bone known as the laminae 20. The laminae 20 fuse with each other to form a spinous process 22. The spinous process 22 provides muscle and ligament attachment.

The transition from the pedicles 16 to the laminae 20 is interrupted by a transverse process 24 that thrust out laterally on each side from the junction of the pedicle 16 and the lamina 20. The transverse processes 24 serve as guides for the attachment of muscles to the vertebrae 12. Connecting the transverse process 24 on each side of the body 14 is a lateral mass 26. Two inferior articular processes 28 extend downward from the junction of the laminae 20 and the transverse processes 24. The inferior articular processes 28 each have a natural bony structure known as an inferior articular facet 32, which faces downward. On the superior articular facet 30 is a superior articulating surface 38. Similarly, a superior articular facet 30 faces upward from the junction of the lateral mass 26 and the pedicle 16. On the inferior articular facet 32 is an inferior articulating surface 40.

Figure 4:
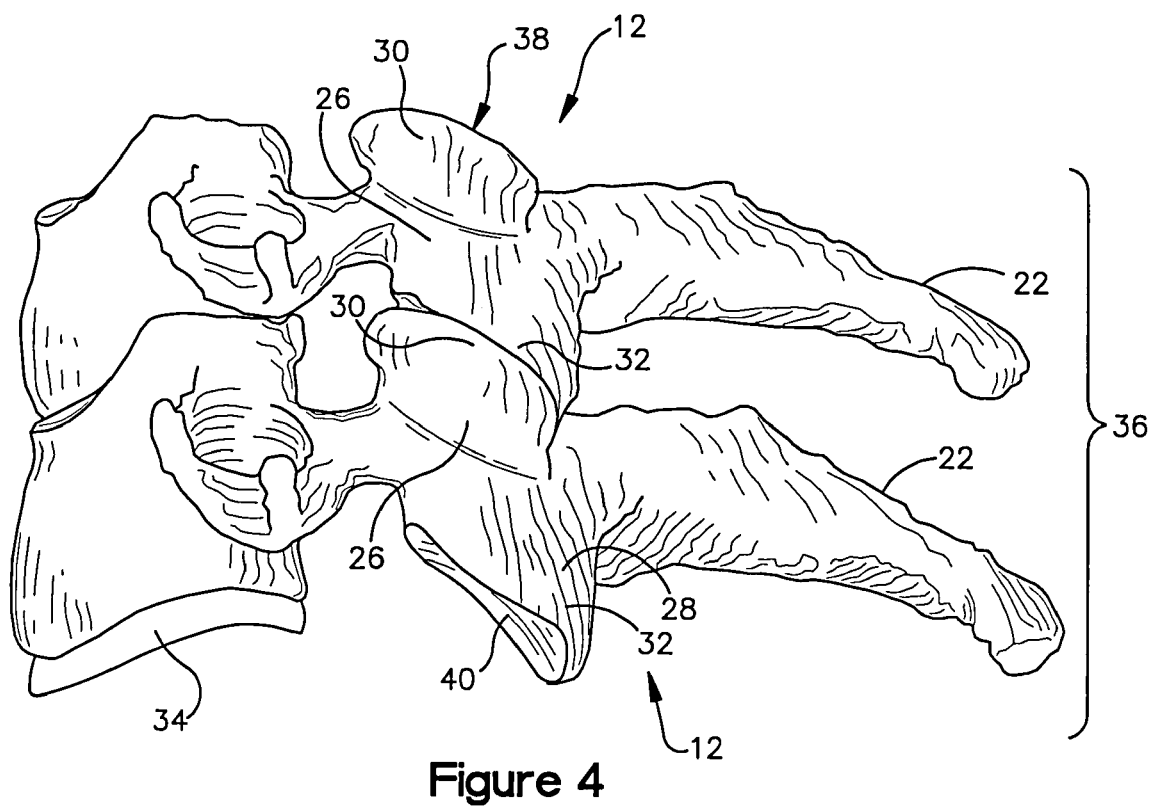
FIG. 4 is a lateral elevation view of a cervical vertebral facet joint.

As shown in FIGS. 3 and 4, when adjacent vertebrae 12 are aligned, the superior articular facet 30 and inferior articular facet 32 interlock. Capped with a smooth articular cartilage, the interlocked vertebrae form a facet joint 36, also known as a zygapophysial joint. An intervertebral disc 34 between each pair of vertebrae 12 permits gliding movement between vertebrae 12. Thus, the structure and alignment of the vertebrae 12 permit a range of movement of the vertebrae 12 relative to each other.

The facet joint 36 is composed of a superior half and an inferior half. The superior half is formed by the vertebral level below the intervertebral disc 34, and the inferior half is formed by the vertebral level above the intervertebral disc 34. For example, in the C3-C4 facet joint, the superior portion of the joint is formed by bony structure on the C4 vertebra (e.g., a superior articular surface and supporting bone on the C4 vertebra), and the inferior portion of the joint is formed by bony structure on the C3 vertebra (e.g., an inferior articular surface and supporting bone on the C3 vertebra).

Figures 5A, 5B, 5C:
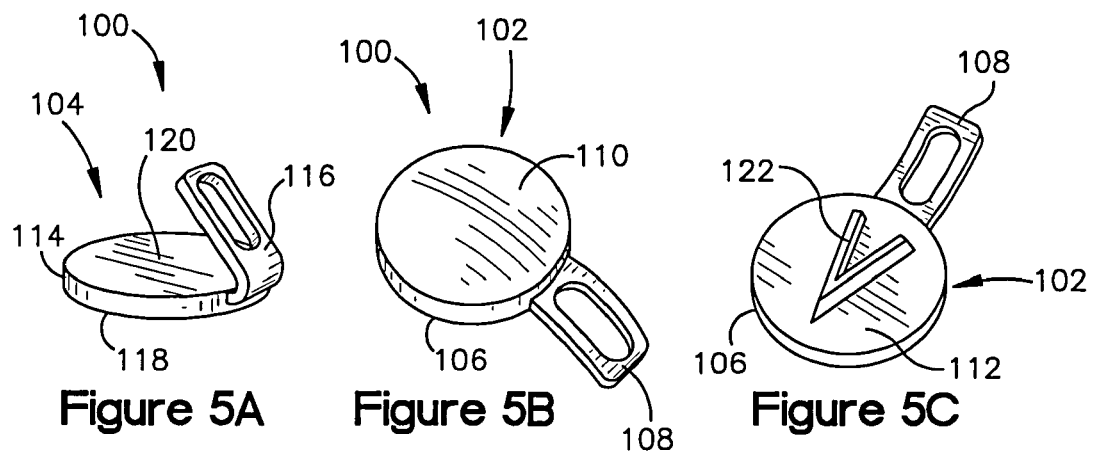
FIG. 5 illustrates a cervical facet implant.

Turning now to FIG. 5, an exemplary cervical facet resurfacing implant according to the present invention is illustrated. The exemplary facet implant 100 generally has a superior implant 102 and an inferior implant 104. The superior implant 102 generally has a disk-shaped portion 106 and a tab 108 extending from the disk-shaped portion 106. The disk-shaped portion 106 includes an articulating surface 110 and a fixation surface 112.

The inferior implant 104 also generally has a disk-shaped portion 114 and a tab 116 extending from the disk-shaped portion 114. The disk-shaped portion 114 includes an articulating surface 118 and a fixation surface 120.

It should be noted that the term "disk-shaped" is not restricted to circular or ovular shapes. A generally disk-shaped implant may have multiple sides, such as a square-shaped, hexagonal-shaped, or octagonal-shaped implant. While each of these shapes appear similar from a lateral perspective and are capable of performing a similar function according to the present invention, a circular or ovular disk-shape is preferred.

Figure 6A:
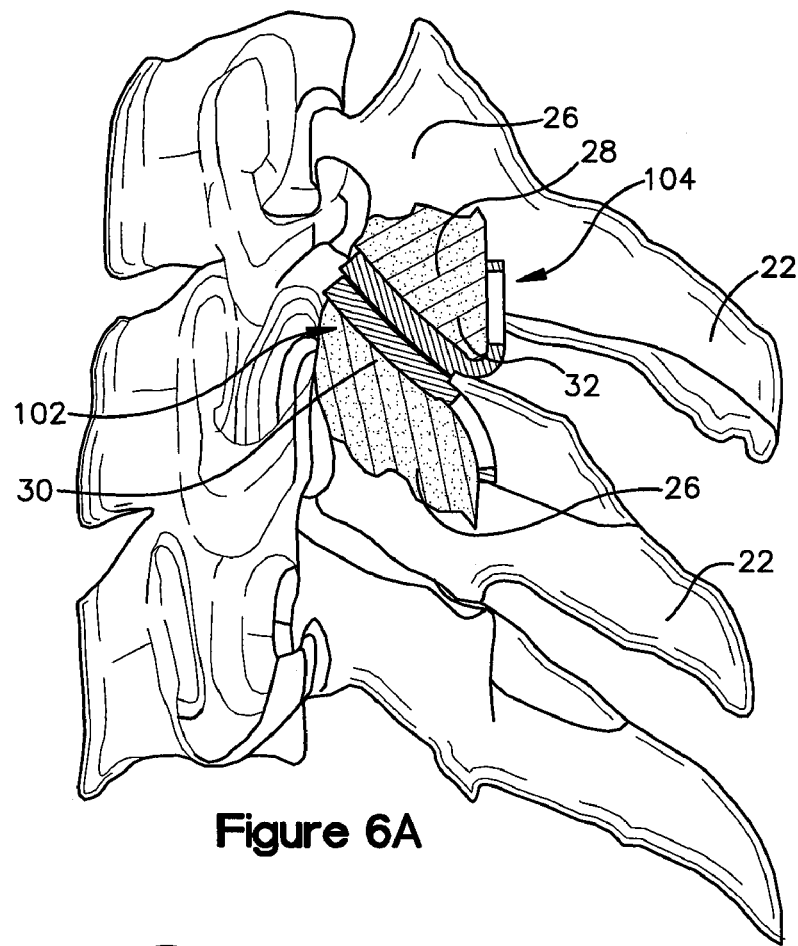
FIGS. 6A-C illustrate a facet implant in conjunction with cervical vertebrae.
Figure 6B:
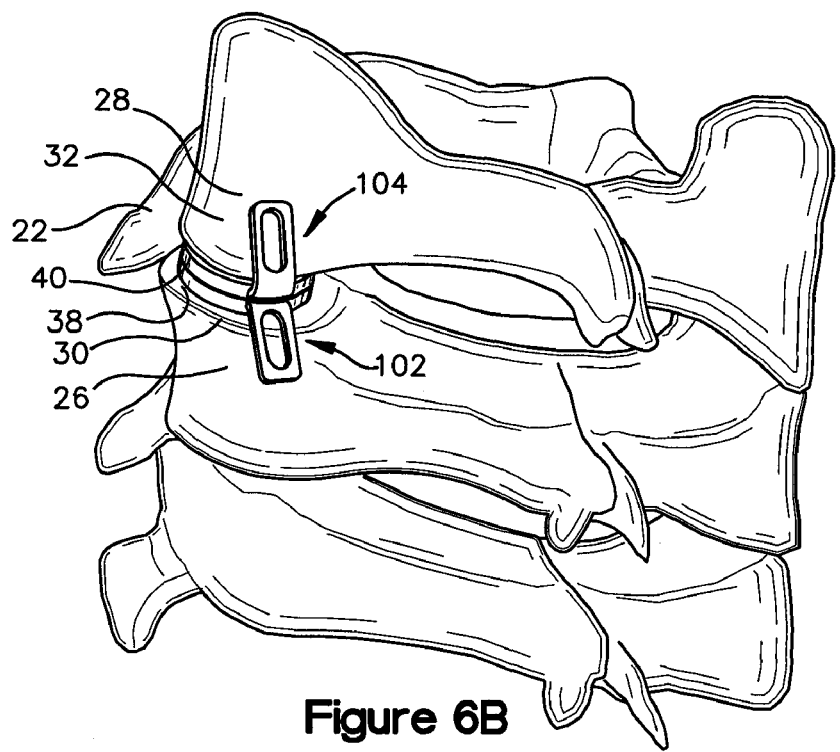
Figure 6C:
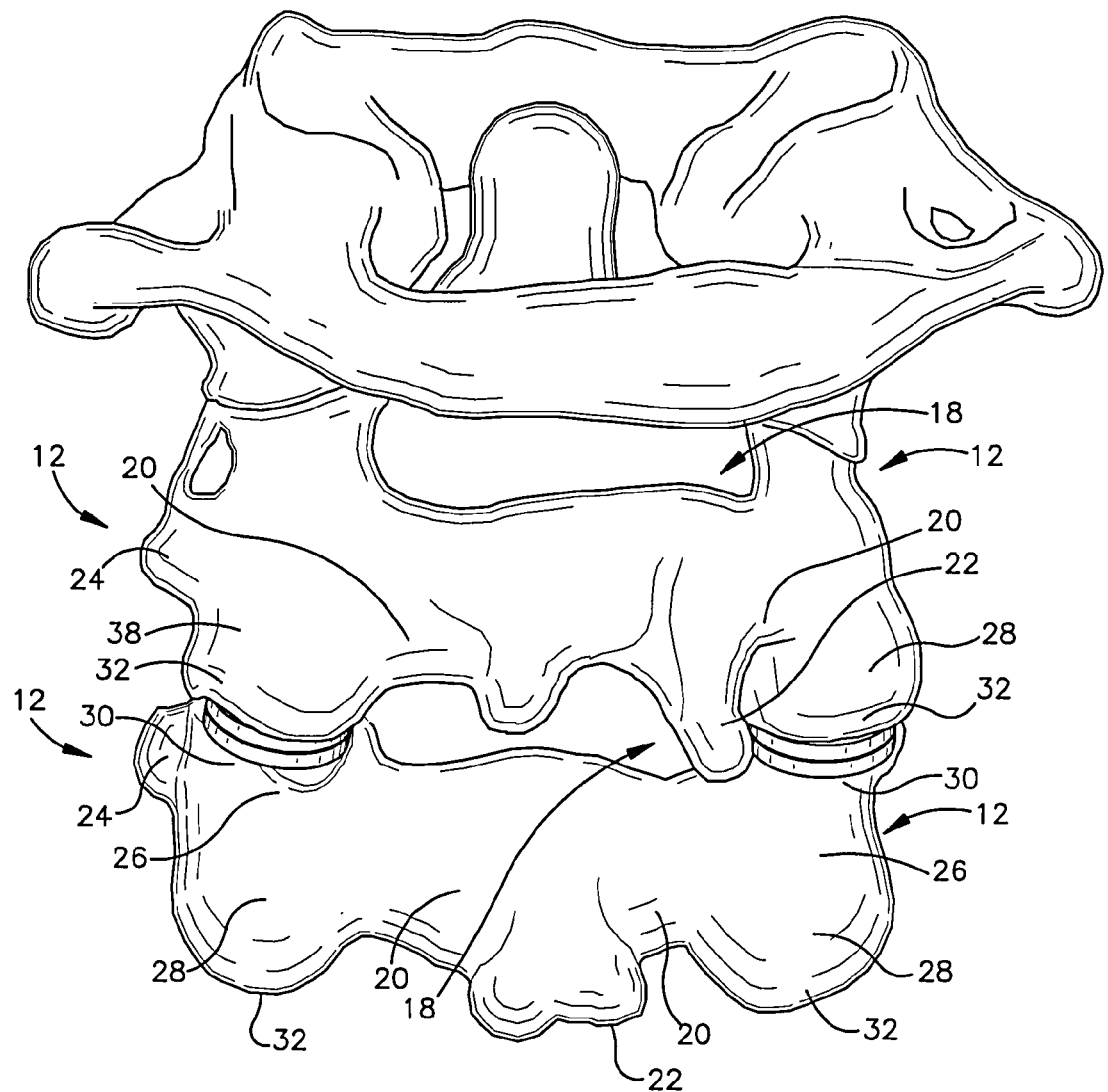

Turning now to FIGS. 6A-C, an exemplary cervical facet resurfacing implant according to the present invention is illustrated in conjunction with a facet joint. The superior implant 102 is configured for placement on superior articular facet 30. The superior implant 102 may be fixed to the superior articulating surface 38 using cemented and/or cementless fixation techniques. In an exemplary embodiment, the superior implant 106 includes a disk-shaped portion 106, which has an articulating surface 110 and a fixation surface 112 and is configured for placement on a specifically prepared superior articulating surface 38.

The disk-shaped portion 106 of the superior implant 102 may range from about 1 mm thick to about 6 mm thick. In an exemplary embodiment, the thickness of the superior implant 102 ranges from about 2 mm to about 4 mm. In another exemplary embodiment, the thickness of the superior implant 102 ranges from about 1.5 mm to about 2.5 mm. The disk-shaped portion 106 of the superior implant 102 may also range from about 3 mm in diameter to about 14 mm in diameter. In an exemplary embodiment, the diameter of the superior implant 102 ranges from about 6 mm to about 12 mm. In another exemplary embodiment, the diameter of the superior implant 102 ranges from about 8 mm to about 10 mm.

The fixation surface 112 may be generally flat or generally curved and is configured to interact with the superior articulating surface 38. The articulating surface 110 may be generally curved and may be configured to interact with an articulating surface 118 of the inferior implant 104.

Extending from the disk-shaped portion 106 of the superior implant is a tab 108 configured to interact with or for attachment to the lateral mass 26 of the vertebra 12. The tab 108 may be generally curved so that it matches the natural curvature of the vertebra 12. For example, the tab 108 and the disk-shaped portion 106 of the superior implant 102 may form an angle ranging from about 110 degrees to about 160 degrees. In one exemplary embodiment, the tab 108 and the disk-shaped portion 106 of the superior implant 102 form an angle ranging from about 120 degrees to about 150 degrees. In another exemplary embodiment, the tab 108 and the disk-shaped portion 106 of the superior implant 102 may form an angle ranging from about 130 degrees to about 145 degrees.

The tab 108 may include a hole or a slot or the like configured to receive a fixation device, such as a screw or the like. In other words, the fixation device passes through the hole or slot of the tab 108 and into the lateral mass 26 of the vertebra 12.

The superior implant 102 may have a surface fixation mechanism for fixing the superior implant 102, such as by fixing the fixation surface 112, to the superior articulating surface 38. The surface fixation mechanism may be any fixation mechanism known in the art, such as at least one of: one or more pegs, one or more pips, ridges, one or more grooves, one or more fins, and one or more screws. In an exemplary embodiment, the surface fixation mechanism includes at least one fin 122. The fin 122 helps prevent the superior implant 102 from migrating along the superior articulating surface. In another exemplary embodiment, the surface fixation mechanism may include a plurality of ridges, grouped in regions such that the ridges in different regions are oriented in different directions. For example, the surface fixation mechanism may include four regions on the fixation surface 112 where each of the four regions has ridges oriented in a different direction. The various orientations of the ridges prevent the inferior implant 104 from moving in different directions with respect to the superior articulating surface 38.

The fixation surface 112 of the superior implant 102 may also have a porous coating; a porous onlay material; a biologic coating; a surface treatment, such as to facilitate bone ingrowth or cement fixation; a material facilitating bone ingrowth; and combinations thereof. For example, the fixation surface 112 may have a porous surface that is beaded, threaded, textured, etc. Further, the fixation surface 112 may have a hydroxyapatite coating or may be plasma-sprayed. In addition to the examples listed, any known method of improving fixation of biologic implants may be used to improve the interaction of the fixation surface 112 and the superior articular facet 30.

In one exemplary embodiment, the fixation surface 112 of the superior implant 102 is configured to interact only with the superior articulating surface 38 and does not interact directly with any other aspect of the superior articular facet 30 or the facet joint 36. The fixation surface 112 of the superior implant 102 may be generally flat or generally curved for improved interaction with the superior articulating surface 38.

The articulating surface 110 in one exemplary embodiment is generally configured to articulate or interact with the articulating surface 118 of the inferior implant 104. Accordingly, the articulating surface 110 of the superior implant 102 may be generally flat or generally curved. The superior implant 102 articulating surface 110 may be configured such that it acts as a "female" surface wherein it is concave or configured to accept a "male" articulating surface 118 of an inferior implant 104. Conversely, the superior implant 102 articulating surface 110 may also be configured such that it acts as a "male" surface wherein it is convex or configured to be accepted by "female" articulating surface 118 of an inferior implant 104.

The superior implant 102 may be composed of any material commonly used in the art for articulating medical implants. Such materials include, but are not limited to, cobalt-chromium alloys, ceramics (alumina ceramic, zirconia ceramic, yttria zirconia ceramic, etc.), titanium, ultra high molecular weight polyethylene (UHMWPE), pyrolytic carbon, titanium/aluminum/vanadium (Ti/Al/V) alloys, Tantalum, Carbon composite materials and combinations thereof. For example, the superior implant 102 may be generally composed of titanium, but have a UHMWPE articulating surface. Some materials are more appropriate for articulating surfaces and some more appropriate for fixation surfaces, but any materials known in the art for use with articulating and fixation surfaces can be used in the present invention. Such materials are commonly used in joint arthroplasty and the like.

The inferior implant 104 is configured for placement on inferior articular facet 32. The inferior implant 104 may be fixed to the inferior articulating surface 40 using cemented and/or cementless fixation techniques. In an exemplary embodiment, the inferior implant 104 has a disk-shaped portion 114, which has an articulating surface 118 and a fixation surface 120 and is configured for placement on a specifically prepared inferior articulating surface 40.

The disk-shaped portion 116 of the inferior implant 104 may range from about 1 mm thick to about 6 mm thick. In an exemplary embodiment, the thickness of the inferior implant 104 ranges from about 2 mm to about 4 mm. In another exemplary embodiment, the thickness of the inferior implant 104 ranges from about 1.5 mm to about 2.5 mm. The disk-shaped portion 114 of the inferior implant 104 may also range from about 3 mm in diameter to about 14 mm in diameter. In an exemplary embodiment, the diameter of the inferior implant 104 ranges from about 6 mm to about 12 mm. In another exemplary embodiment, the diameter of the inferior implant 104 ranges from about 8 mm to about 10 mm.

The fixation surface 120 may be generally flat or generally curved and is configured to interact with the inferior articulating surface 40. The articulating surface 118 may be generally curved and may be configured to interact with an articulating surface 110 of the superior implant 104.

Extending from the disk-shaped portion 114 of the inferior implant is a tab 116 configured to interact with or for attachment to the inferior articular process 28 of the vertebra 12. The tab 116 may be generally curved so that it matches the natural curvature of the vertebra 12. For example, the tab 116 and the disk-shaped portion 114 of the inferior implant 104 may form an angle ranging from about 10 degrees to about 70 degrees. In one exemplary embodiment, the tab 116 and the disk-shaped portion 114 of the inferior implant 104 form an angle ranging from about 20 degrees to about 60 degrees. In another exemplary embodiment, the tab 116 and the disk-shaped portion 114 of the inferior implant 104 may form an angle ranging from about 30 degrees to about 50 degrees.

The tab 116 may include a hole or a slot or the like configured to receive a fixation device, such as a screw or the like. In other words, the fixation device passes through the hole or slot of the tab 116 and into the inferior articular process 28 of the vertebra 12.

The inferior implant 104 may have a surface fixation mechanism for fixing the inferior implant 104, such as by fixing the fixation surface 120, to the inferior articulating surface 40. The surface fixation mechanism may be any fixation mechanism known in the art, such as at least one of: one or more pegs, one or more pips, ridges, one or more grooves, one or more fins, and one or more screws. In an exemplary embodiment, the surface fixation mechanism includes at least one fin, such as the fin shown as 122 on the superior implant 102. The fin helps prevent the inferior implant 104 from migrating along the superior articulating surface. In another exemplary embodiment, the surface fixation mechanism may include a plurality of ridges, grouped in regions such that the ridges in different regions are oriented in different directions. For example, the surface fixation mechanism may include four regions on the fixation surface 120 where each of the four regions has ridges oriented in a different direction. The various orientations of the ridges prevent the inferior implant 104 from moving in different directions with respect to the inferior articulating surface 40.

The fixation surface 120 of the inferior implant 104 may also have a porous coating; a porous onlay material; a biologic coating; a surface treatment, such as to facilitate bone ingrowth or cement fixation; and combinations thereof. For example, the fixation surface 120 may have a porous surface that is beaded, threaded, textured, etc. Further, the fixation surface 120 may have a hydroxyapatite coating or may be plasma-sprayed. In addition to the examples listed, any known method of improving fixation of biologic implants may be used to improve the interaction of the fixation surface 120 and the inferior articular facet 32.

In one exemplary embodiment, the fixation surface 120 of the inferior implant 104 is configured to interact only with the inferior articulating surface 40 and does not interact directly with any other aspect of the inferior articular facet 32, the inferior articular process 28, or even the facet joint 36. The fixation surface 120 of the inferior implant 104 may be generally flat or generally curved for improved interaction with the inferior articulating surface 40.

The articulating surface 118 in one exemplary embodiment is generally configured to articulate or interact with the articulating surface 110 of the superior implant 102. Accordingly, the articulating surface 118 of the inferior implant 104 may be generally flat or generally curved. The inferior implant 104 articulating surface 118 may be configured such that it acts as a "female" surface wherein it is concave or configured to accept a "male" articulating surface 110 of a superior implant 102. Conversely, the inferior implant 104 articulating surface 118 may also be configured such that it acts as a "male" surface wherein it is convex or configured to be accepted by "female" articulating surface 110 of an superior implant 102.

The inferior implant 104 may be composed of any material commonly used in the art for articulating medical implants. Such materials include, but are not limited to, cobalt-chromium alloys, ceramics (alumina ceramic, zirconia ceramic, yttria zirconia ceramic, etc.), titanium, ultra high molecular weight polyethylene (UHMWPE), pyrolytic carbon, titanium/aluminum/vanadium (Ti/Al/V) alloys, and combinations thereof. For example, the inferior implant 104 may be generally composed of a ceramic material or a cobalt-chromium alloy. Some materials are more appropriate for articulating surfaces and some more appropriate for fixation surfaces, but any materials known in the art for use with articulating and fixation surfaces can be used in the present invention. Such materials are commonly used in joint arthroplasty and the like.

Figure 7:
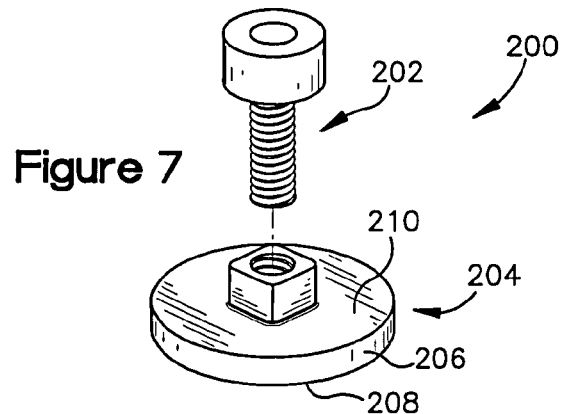
FIG. 7 illustrates an alternate embodiment of a cervical facet inferior implant in conjunction with a trans-lateral mass screw.

Turning next to FIG. 7, there is provided an alternate embodiment 200 of a cervical facet inferior implant in conjunction with a trans-lateral mass screw. In another exemplary embodiment, the inferior implant 204 is configured to interact with or attach to a trans-lateral mass fixation mechanism 202. As shown, the trans-lateral mass fixation mechanism 202 is a screw, but may be any like fixation mechanism. For example, the inferior implant 204 may include a threaded hole 212 either extending from or bored into the fixation surface 210 of the inferior implant 204. The manner in which the inferior implant 204 and the trans-lateral mass fixation mechanism 202 interact may vary with different anatomies. For example, it may be preferable to offset the trans-lateral mass screw 202 from the inferior implant 204 such that when the trans-lateral mass screw 202 and inferior implant 204 interact, the trans-lateral mass screw 202 is not perpendicular to the inferior implant 204. The trans-lateral mass screw 202 may range from about 0 degrees offset from perpendicular to about 60 degrees offset from perpendicular.

The articulating surface 208 of the inferior implant 204 is generally configured to articulate or interact with the articulating surface 110 of the superior implant 102 shown in FIG. 5. Accordingly, the articulating surface 208 of the inferior implant 204 may be generally flat or generally curved. The inferior implant 204 articulating surface 208 may be configured such that it acts as a "male" surface wherein it is convex or configured to be accepted by a "female" articulating surface 110 of a superior implant 102. Conversely, the inferior implant 204 articulating surface 208 may also be configured such that it acts as a "female" surface wherein it is configured to accept a "male" articulating surface 110 of a superior implant 102.

A trans-lateral mass fixation mechanism 202 is configured to interact with the inferior implant 204. The trans-lateral mass fixation mechanism 202 secures the inferior implant 204 to the inferior articular facet 32. The trans-lateral mass fixation mechanism 202 may be any fixation mechanism known in the art, such as a translaminar screw. The trans-lateral mass fixation mechanism 202 may be made from any material known in the art for medical fixation devices. For example, the trans-lateral mass fixation mechanism 202 may be made from titanium, titanium/aluminum/vanadium (Ti/Al/V) alloys, Tantalum, CrCo, ceramic, carbon or carbon composite materials.

Figure 8:
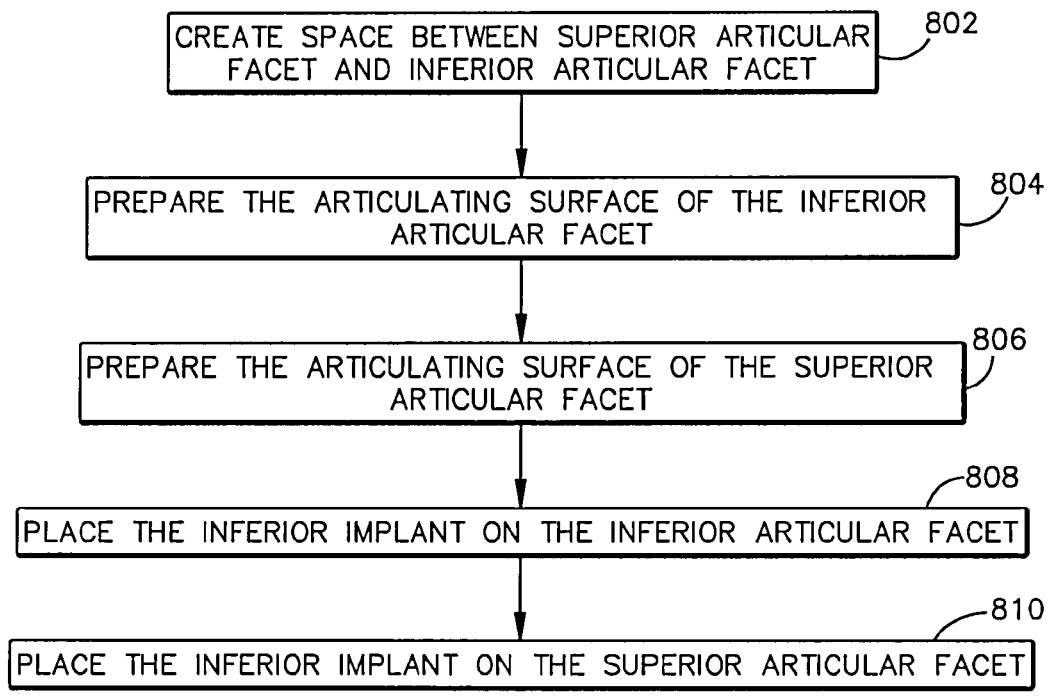
FIG. 8 is a flow chart generally illustrating a method for providing articulating surfaces for cervical facet joint articular facets.

Turning next to FIG. 8, there is provided a flow diagram generally illustrating a method for providing articulating surfaces for facet joint articular facets. The overall flow begins at process block 802 wherein a space is created between the superior articular facet 30 and the inferior articular facet 32. It will be understood by those skilled in the art that prior to creating the space, it may be preferable or even necessary to expose the facet joint 36 at an effected level and remove the capsule. The effected level may be exposed through use of any appropriate procedure, such as a modified "Wiltse" approach. The creation of the space at process block 602 may be accomplished by using a curette or similar device and by removing the cartilaginous surfaces of the facet joint 36. In one exemplary embodiment, the created space is sufficient for using a rasp on an articulating surface of an articular facet. The space created between the superior articular facet 30 and the inferior articular facet 32 may range, for example, from about 2 mm to about 15 mm. In one exemplary embodiment, the space ranges from about 4 mm to about 8 mm. It should be understood that a rasp can be any tool used to scrape, grate, or file the facets.

Flow progresses to process block 804 wherein the articulating surface 40 of the inferior articular facet 32 is prepared for an inferior implant 104. Such preparation may be made by a rasp, such as a rasp specifically designed for preparing a surface for the cervical facet implant. Progression then continues to process block 806 wherein the articulating surface 38 of the superior articular facet 30 is prepared for a superior implant 102. Again, such preparation may be made by a rasp, such as a rasp specifically designed for preparing a surface for the cervical facet implant.

Figure 10:
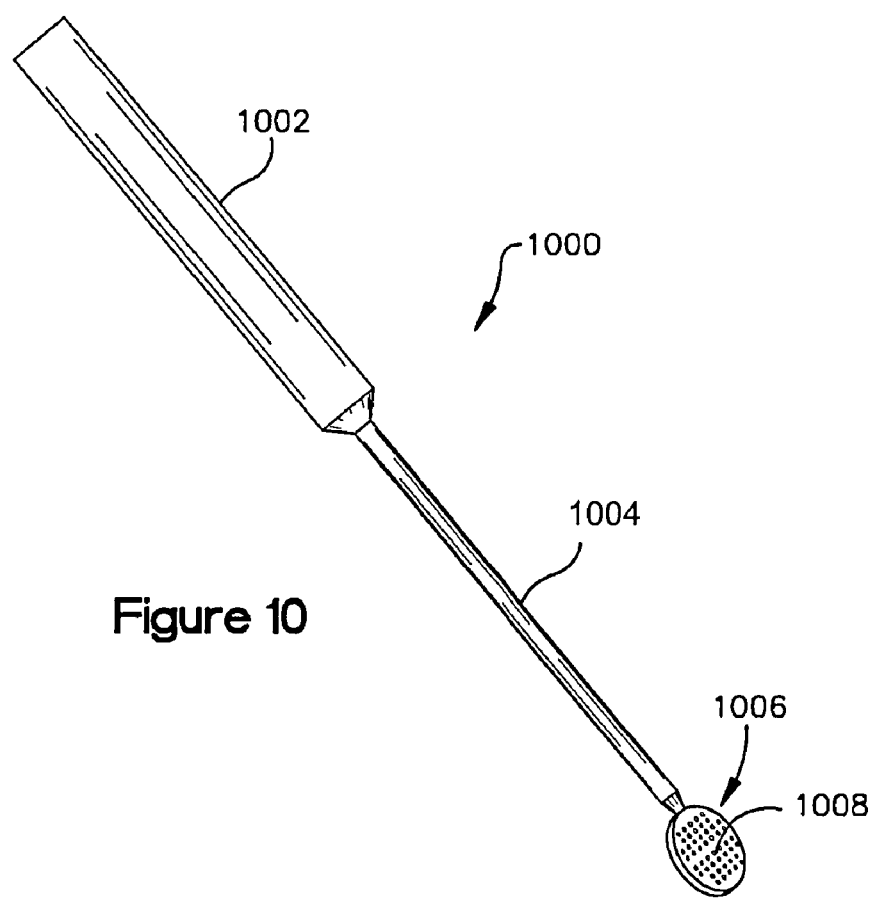
FIG. 10 is an illustration of a rasp.
Figure 11:
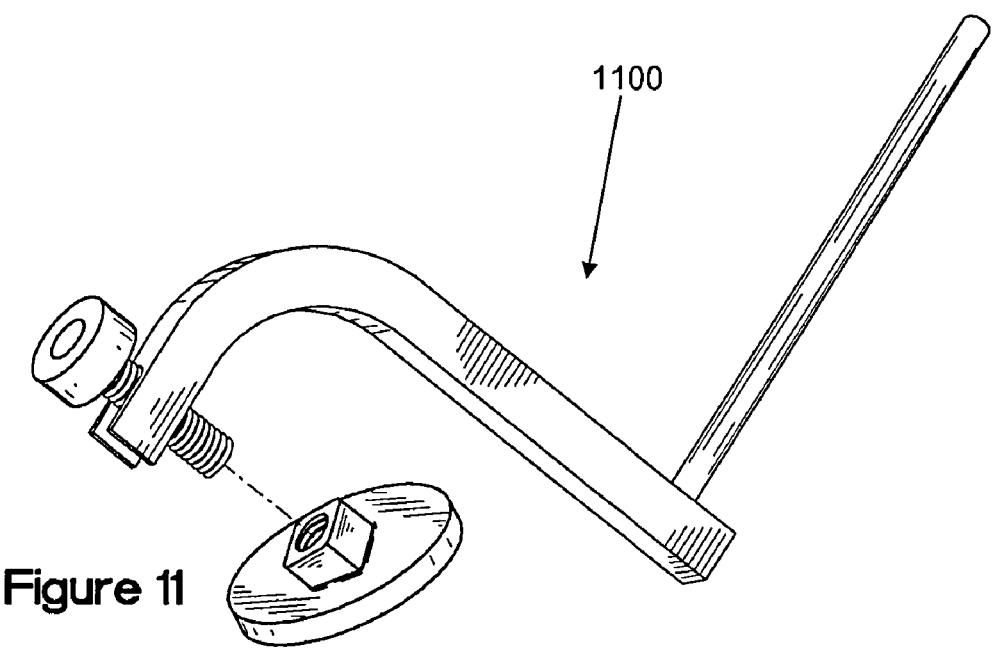
FIG. 11 is an illustration of an aiming device for use in positioning a trans lateral mass screw.

Each of the rasps of process blocks 804 and 806 may be either a single shaft rasp or a double action rasp, such as those illustrated in FIGS. 10-12 and described in detail herein. The process of preparing the articulating surfaces 38 and 40 of the articular facets 28 and 30 may involve using multiple rasps of increasing thickness while widening the space created in process block 802. For example, a 2 mm rasp may initially be used, then a 4 mm rasp, then a 6 mm rasp, then an 8 mm rasp, etc., until a desired result is achieved. In addition, the rasps of process blocks 804 and 806 may be the same rasp. Further, a single rasp can be used to prepare the articulating surfaces 38 and 40 concurrently. The articulating surfaces 38 and 40 may be prepared such that a bleeding bone bed is created to facilitate bone ingrowth for the superior implant 102 and inferior implant 104.

Figure 9:
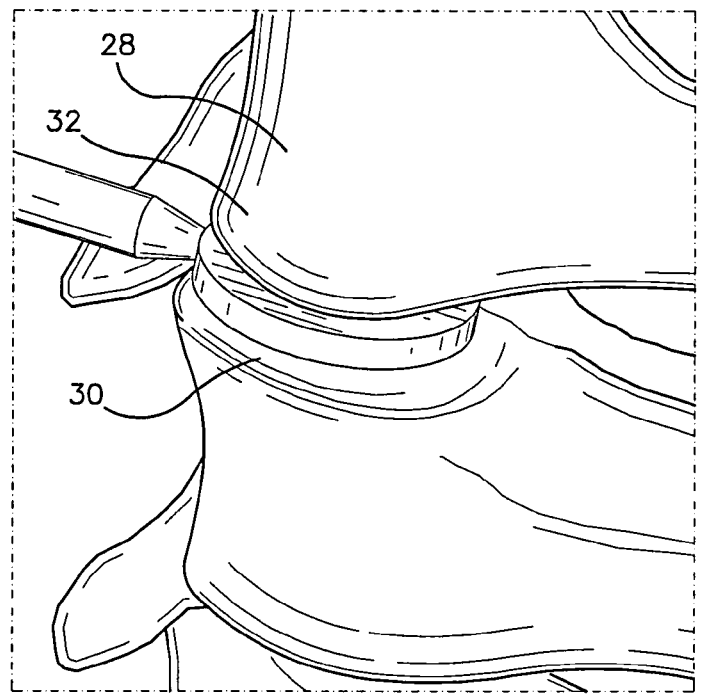
FIG. 9 is an illustration of a rasp being used to prepare an articulating surface.

As shown in FIG. 9, when the single handed rasp is used to prepare articulating surface 38 and/or articulating surface 40, the working end of the tool may be positioned inside the space created in process block 802. The rasp may then be moved from an anterior to a posterior position inside the facet joint 36 in order to effect a clean and uniform resection of the created space in the shape and dimension of both implants. In other words, the articulating surface 38 is prepared such that its shape and dimension resembles the superior implant 102 and the articulating surface 40 is prepared such that its shape and dimension resembles the inferior implant 104. The anterior/posterior movement of the rasp may be continued until the rasp is too small for the space created. The rasp may be too small when the space created is so wide that the rasp cannot prepare both the articulating surfaces 38 and 40 concurrently. A larger (thicker) rasp may then be used. Increasingly larger rasps may be used until the created space is increased such that it ranges from about 4 mm to about 8 mm. In one exemplary embodiment, the rasps are designed to cut only when moving in a posterior direction to help prevent injury during the resurfacing process.

In one embodiment, the steps of process blocks 802, 804 and 806 are repeated on the contralateral side of facet joint 36 prior to performing the steps of process block 808.

Progression then flows to process block 808 wherein the inferior implant 104 is placed on the prepared/resurfaced articulating surface 40 of the inferior articular facet 32. In one exemplary embodiment, the inferior implant 104 is placed such that the disk-shaped portion 114 interacts with the articulating surface 40 of the inferior articular facet 32, but not with other aspects of the inferior articular facet 32.

In one alternative embodiment, a trans-lateral mass screw 202 is used to secure an inferior implant 204 to the inferior articular facet 32. In this embodiment, the above method would also include using the trans-lateral mass screw 202 to secure the inferior implant 204 to the inferior articular facet 32.

To facilitate placement of the trans-lateral mass screw 106, an aiming device such as the device illustrated in FIG. 11 may be used. The aiming device 1100 can be used to position a drill for creating a trans-lateral mass hole for the trans-lateral mass screw 202. A drill can then be used to create the hole, which may have a diameter of about 2 mm, depending on the diameter of the trans-lateral mass screw 202. Once the hole is drilled, the trans-lateral mass screw 202 can be introduced into the hole and then used to secure the inferior implant 104 to the inferior articular facet 32.

In one embodiment, the steps of process blocks 808, including any steps associated with the drilling or placement of the trans-lateral mass screw 202, are repeated on the contralateral side of facet joint 36 prior to performing the steps of process block 810.

Progression then continues to process block 810 wherein the superior implant 102 is placed on the prepared/resurfaced articulating surface 38 of the superior articular facet 30. In one exemplary embodiment, the superior implant 102 is placed such that the disk-shaped portion 106 interacts with the articulating surface 38 of the superior articular facet 30, but not with other aspects of the superior articular facet 30.

In one embodiment, the steps of process blocks 802, 804, 806, 808 and 810 are then repeated on the contralateral side.

Turning now to FIG. 10, a single handed rasp is illustrated. The rasp 1000 includes a handle 1002 and a shaft 1004 connecting the handle 1002 to the working end of the rasp 1000. Attached to the shaft 1004 at the working end of the rasp 1000 is a head 1006. The head 1006 has at least one cutting surface 1008. In one exemplary embodiment, the cutting surface 1008 is configured to cut when the cutting surface 1008 is moved in a first direction (e.g. when the rasp is moved from the anterior to the posterior direction of the facet joint) but not when the cutting surface 1008 is moved in a direction opposite to the first direction (e.g. when the rasp is moved from the posterior to the anterior direction of the facet joint).

The rasp 1000 is configured to prepare the articulating surfaces of a facet joint. In an exemplary embodiment, the rasp 1000 is configured to prepare articulating surfaces 38 and 40 of the articular facets 28 and 30 such that the shape and dimension of the prepared articulating surfaces resembles the shape and dimension of the superior implant 102 and inferior implant 104. For example, if the superior implant 102 and/or inferior implant 104 are curved, the head 1006 may be generally curved to properly prepare the surface for the implant.

In addition, the rasp 1000 may be made from any appropriate material commonly used for medical tools. In one exemplary embodiment, at least part of the rasp 1000 is made from titanium, although the rasp could also be made from any material known in the art.

While the present invention has been described in association with several exemplary embodiments, the described embodiments are to be considered in all respects as illustrative and not restrictive. Such other features, aspects, variations, modifications, and substitution of equivalents may be made without departing from the spirit and scope of this invention which is intended to be limited solely by the scope of the following claims. Also, it will be appreciated that features and parts illustrated in one embodiment may be used, or may be applicable, in the same or in a similar way in other embodiments.

What is claimed is:

1. A method for providing articulating surfaces for cervical vertebrae facet joint articular facets comprising:

creating a space between a superior articular facet of a selected cervical vertebra and an inferior articular facet of a cervical vertebra immediately above the selected vertebra;

fixing a generally flat inferior implant having a fixation surface and a generally flat articulating surface on the inferior articular facet such that the fixation surface of the inferior implant interacts with an articulating surface of the inferior articular facet; and fixing a generally flat superior implant having a fixation surface and a generally flat articulating surface on the superior articular facet such that the fixation surface of the superior implant interacts with an articulating surface of the superior articular facet;

wherein the articulating surface of the superior implant forms the majority of the top surface of the superior implant and the articulating surface of the inferior implant forms the majority of the bottom surface of the inferior implant; and wherein the articulating surface of the superior implant and the articulating surface of the inferior implant are positioned to directly contact and articulate with one another following the fixation of the superior implant to the superior articular facet and fixation of the inferior implant to the inferior articular facet.

2. The method of claim 1 further comprising performing each of the steps of claim 1 on a contralateral side of the facet joint.

3. The method of claim 1 further comprising:
using an inferior facet rasp to prepare the articulating surface of the inferior articular facet for the inferior implant; and
using a superior facet rasp to prepare the articulating surface of the superior articular facet for the superior implant.

4. The method of claim 1 wherein a curette is used to begin the step of creating the space.

5. The method of claim 3 wherein the created space is sufficient for using at least one of the inferior facet rasp or the superior facet rasp on the articulating surface of an articular facet.

6. The method of claim 1 wherein the created space ranges from about 2 mm to about 15 mm.

7. The method of claim 3 wherein the inferior facet rasp and the superior facet rasp are the same rasp.

8. The method of claim 3 wherein multiple rasps of increasing thickness are used to prepare the articulating surfaces of the inferior and superior articular facets.

9. The method of claim 3 wherein preparing the articulating surfaces of the inferior and superior articular facets causes the created space to be increased to accommodate the superior implant and the inferior implant.

10. The method of claim 3 wherein the articulating surfaces of the inferior and superior articular facets are prepared such that the shape of the prepared articulating surface of the superior articular facet resembles the superior implant and the shape of the prepared articulating surface of the inferior articular facet resembles the inferior implant.

11. The method of claim 3 wherein preparing the articulating surfaces of the inferior and superior articular facets creates a bleeding bone bed to facilitate bone ingrowth at the articulating surfaces of the inferior and superior articular facets.

12. The method of claim 3 wherein at least one of the inferior facet rasp or the superior facet rasp is configured to cut when moving in a first direction, but not when moving in a direction opposite of the first direction.

13. The method of claim 1 wherein the step of fixing the inferior implant on the inferior articular facet comprises using a trans-lateral mass fixation mechanism.

14. A method for providing articulating surfaces for cervical vertebrae facet joint articular facets comprising:
creating a space of from about 4 mm to about 15 mm between a superior articular facet of a selected cervical vertebra and an inferior articular facet of a cervical vertebra immediately above the selected vertebra;
placing a generally flat disk-shaped inferior implant having a fixation surface and a generally flat articulating surface in the created space;
fixing the inferior implant on the inferior articular facet such that the fixation surface of the inferior implant interacts with an articulating surface of the inferior articular facet;
placing a generally flat disk-shaped superior implant having a fixation surface and a generally flat articulating surface in the created space; and
fixing the superior implant on the superior articular facet such that the fixation surface of the superior implant interacts with an articulating surface of the superior articular facet;
wherein the articulating surface of the superior implant forms the majority of the top surface of the superior implant and the articulating surface of the inferior implant forms the majority of the bottom surface of the inferior implant; and
wherein the articulating surface of the superior implant and the articulating surface of the inferior implant are positioned to directly contact and articulate with one another following the fixation of the superior implant to the superior articular facet and fixation of the inferior implant to the inferior articular facet.

15. The method of claim 14 further comprising performing each of the steps of claim 14 on a contralateral side of the facet joint.

16. The method of claim 14 wherein a curette is used to begin the step of creating the space.

17. The method of claim 14 further comprising using an inferior facet rasp to prepare the articulating surface of the inferior articular facet for the inferior implant and using a superior facet rasp to prepare the articulating surface of the superior articular facet for the superior implant.

18. The method of claim 17 wherein the inferior facet rasp and the superior facet rasp are the same rasp.

19. The method of claim 17 wherein multiple rasps of increasing thickness are used to prepare the articulating surfaces of the inferior and superior articular facets.

20. The method of claim 17 wherein preparing the articulating surfaces of the inferior and superior articular facets causes the created space to be increased to accommodate the superior implant and the inferior implant.

21. The method of claim 17 wherein preparing the articulating surfaces of the inferior and superior articular facets creates a bleeding bone bed to facilitate bone ingrowth at the articulating surfaces of the inferior and superior articular facets.

22. The method of claim 17 wherein at least one of the inferior facet rasp or the superior facet rasp is configured to cut when moving in a first direction, but not when moving in a direction opposite of the first direction.

23. The method of claim 14 wherein the step of fixing the inferior implant on the inferior articular facet comprises using a trans-lateral mass fixation mechanism.

* * * * *